US011386552B2

(12) United States Patent
Russell et al.

(10) Patent No.: US 11,386,552 B2
(45) Date of Patent: Jul. 12, 2022

(54) SYSTEM AND METHOD TO INTERPRET TESTS THAT CHANGE COLOR TO INDICATE THE PRESENCE OR NON-PRESENCE OF A COMPOUND

(71) Applicant: GENPRIME, INC., Spokane, WA (US)

(72) Inventors: Michael Arthur Russell, Spokane, WA (US); Jason Buck Somes, Spokane, WA (US); Darby Dawn McLean, Spokane Valley, WA (US); Claire Elizabeth Norton, Spokane, WA (US)

(73) Assignee: GENPRIME, INC., Spokane, WA (US)

( * ) Notice: Subject to any disclaimer, the term of this patent is extended or adjusted under 35 U.S.C. 154(b) by 833 days.

(21) Appl. No.: 16/322,844

(22) PCT Filed: Jul. 31, 2017

(86) PCT No.: PCT/US2017/044726
§ 371 (c)(1),
(2) Date: Feb. 1, 2019

(87) PCT Pub. No.: WO2018/026725
PCT Pub. Date: Feb. 8, 2018

(65) Prior Publication Data
US 2021/0374946 A1 Dec. 2, 2021

Related U.S. Application Data

(60) Provisional application No. 62/369,588, filed on Aug. 1, 2016.

(51) Int. Cl.
G06K 9/00 (2022.01)
G06T 7/00 (2017.01)
(Continued)

(52) U.S. Cl.
CPC ........... *G06T 7/0012* (2013.01); *G01N 21/78* (2013.01); *G06T 7/90* (2017.01);
(Continued)

(58) Field of Classification Search
None
See application file for complete search history.

(56) References Cited

U.S. PATENT DOCUMENTS

2002/0136436 A1    9/2002  Schrier et al.
2009/0060303 A1    3/2009  Douglass et al.
(Continued)

FOREIGN PATENT DOCUMENTS

JP   H09257708 A    10/1997
WO      0046598 A1   8/2000

OTHER PUBLICATIONS

Filippini, Daniel, and Ingemar Lundström. "Measurement strategy and instrumental performance of a computer screen photo-assisted technique for the evaluation of a multi-parameter colorimetric test strip." Analyst 131.1 (2006): 111-117. (Year: 2006).*

(Continued)

Primary Examiner — Sean M Conner
(74) Attorney, Agent, or Firm — Cozen O'Connor

(57) ABSTRACT

A specimen analysis system includes at least one processor to receive image information that represents a respective plurality of pixels of an image of each of a plurality of testing areas to indicate the presence or absence of a test subject compound; to determine for each testing area a number of pixels that indicates either the presence or the absence of the test subject compound, if the number of pixels indicating positive for each of a plurality of testing areas equals or exceeds a first minimum threshold value indicating that the testing area is positive for either the presence or absence of the test subject compound, totaling (Continued)

all testing areas indicating positive for either the presence or absence of the test subject compound, and if the total number of the testing areas indicating positive for either the presence or absence of the test subject compound equals or exceeds a second minimum threshold value indicating an overall positive test result for either the presence or absence of the test subject compound.

20 Claims, 7 Drawing Sheets

(51) Int. Cl.
  *G06T 7/90* (2017.01)
  *G01N 21/78* (2006.01)
(52) U.S. Cl.
  CPC .............. *G06T 2207/10024* (2013.01); *G06T 2207/30024* (2013.01); *G06T 2207/30242* (2013.01)

(56) References Cited

U.S. PATENT DOCUMENTS

| | | | |
|---|---|---|---|
| 2011/0076781 A1* | 3/2011 | Liu | G01N 35/00029 |
| | | | 422/68.1 |
| 2013/0183772 A1 | 7/2013 | Fleming et al. | |
| 2015/0141268 A1 | 5/2015 | Rothberg et al. | |
| 2019/0094116 A1* | 3/2019 | Cheng | G06V 10/25 |

OTHER PUBLICATIONS

Extended European Search Report, dated Dec. 10, 2019, for European Application No. 17837479.9-1210, 8 pages.
Carrio et al., "Automated Low-Cost Smartphone-Based Lateral Flow Saliva Test Reader for Drugs-of-Abuse Detection," *Sensors* 15:29569-29593, 2015.
International Search Report from International Application No. PCT/US2017/044726, dated Nov. 7, 2017, 4 pages.
Written Opinion from International Application No. PCT/US2017/044726, dated Nov. 7, 2017, 7 pages.

* cited by examiner

400

| REFERENCE COLOR COMPONENT VALUES | SPECIMEN VALIDITY CHARACTERISTIC | 404 |
|---|---|---|
| 50, 40, 30 | RESULT A | 420 |
| 100, 100, 100 | RESULT B | 422 |
| 150, 200, 220 | RESULT C | 424 |

| REFERENCE COLOR COMPONENT VALUES | PHYSICAL CHARACTERISTIC VALUE | SPECIMEN VALIDITY STATUS |
|---|---|---|
| 20, 34, 40 | VALUE 1 | INVALID |
| 50, 40, 30 | VALUE 2 | VALID |
| 100, 100, 100 | VALUE 3 | VALID |
| 150, 200, 220 | VALUE 4 | INDETERMINATE |

SYSTEM AND METHOD TO INTERPRET TESTS THAT CHANGE COLOR TO INDICATE THE PRESENCE OR NON-PRESENCE OF A COMPOUND

BACKGROUND

Technical Field

The present disclosure generally relates to specimen analysis systems and, more particularly, to specimen analysis systems that optically assess specimen test articles.

Description of the Related Art

Specimen test articles may be used to determine a presence or absence of a test subject substance in a specimen (i.e., the principal substance for which the specimen is being tested). In particular, certain specimen test articles (e.g., lateral flow strips) include at least one optical test substance marker that optically indicates at least the presence or absence of the test subject substance in the specimen. For example, a color of the optical test substance marker may indicate the presence or absence of the test subject substance within the specimen. As one example, a color of the optical test substance marker may remain unchanged from a first color if the specimen does not contain the test subject substance, while the color of the optical test substance marker changes from the first color to a second, different color if the test subject substance is present within the specimen.

Colorimetric response tests have been traditionally interpreted visually by a human operator. The resulting test colors of such colorimetric tests, however, can vary greatly in color intensity, thus leading to a highly subjective user interpretation. For example, one such colorimetric test is a Guaiac test used to detect hemoglobin in a fecal sample. The Guaiac test indicates the presence of hemoglobin by turning blue. In some instances, positive results may be indicated by indistinct blue auras surrounding the specimen test area. In some cases, operators may interpret this aura as sufficient to indicate a positive result. Other operators may interpret this aura as insufficient to indicate a positive result. In addition, colorimetric analysis typically includes multiple test areas that must indicate a positive response for a positive indication to be found. This is done to minimize false-positive results. However, some operators may nevertheless interpret a positive result when a vibrant colorimetric response is detected in only a single test area.

Therefore, there is a continuing need for system and method for accurately and objectively determining the results of a colorimetric test regardless of the operator who interprets the colorimetric test.

BRIEF SUMMARY

Colorimetric testing devices can be used to determine the presence or non-presence of a compound. Briefly, and in general terms, system and methods are used to detect the intensity of a colorimetric change of a plurality of pixels in a plurality of testing areas. If a specified number of pixels in each of a specified number of the multiple testing areas satisfy a designated hue, saturation and/or brightness criteria, a positive overall test result is indicated.

A specimen analysis system to analyze specimen test articles that include a plurality of testing areas that indicate at least a presence or an absence of a test subject compound in a specimen, the specimen analysis system may be summarized as including: at least one processor; and at least one non-transitory processor-readable medium that is communicatively coupled to the at least one processor and that stores at least one of processor-executable instructions or data that, when executed by the at least one processor, cause the at least one processor to: receive a set of image information that represents an image of each of the plurality of testing areas, each of the testing areas represented by a respective plurality of pixels in the set of image information; for each of the plurality of testing areas, determine a number of pixels that indicate as positive for the presence of the test subject compound; for each of the testing areas, determine if the number of pixels that indicate as positive equals or exceeds a first minimum threshold value which indicates that the testing area is positive for the presence of the test subject compound; determine a number of testing areas that indicate positive for the presence of the test subject compound; and determine if the number of testing areas that indicate positive for the presence of the test subject compound equals or exceeds a second minimum threshold value which indicates an overall positive test result for the presence of the test subject compound.

The specimen analysis system may further include at least one output device that outputs the overall test results. To determine the positive indication of the plurality of pixels for the presence of the test subject compound the processor may assess the intensity of a colorimetric change of the pixels. To assess the intensity of a colorimetric change the processor may assess criteria taken from the group consisting of hue, saturation and brightness or any combination thereof. The specimen test article may include a colorimetric specimen test. The colorimetric specimen test may be a Guaiac test. The test subject compound may be hemoglobin. The plurality of pixels may be determined to indicate as positive in the presence of the hemoglobin. The plurality of pixels may be blue in the presence of the hemoglobin. The plurality of testing areas may be six. Five of the six testing areas may be determined to indicate as positive to achieve an overall positive test result indicating the presence of the subject test compound. All of the plurality of testing areas may be determined to indicate as positive to achieve an overall positive test result indicating the presence of the subject test compound. A number of false-positive overall test results may be minimized. The specimen test article may further include an optical specimen validity marker, the color of which may indicate the validity of the specimen. The processor may receive an image of the optical specimen validity marker and determine the validity of the specimen based upon the color of the pixels in the image.

A computer-implemented method to analyze specimen test articles that include a plurality of testing areas that indicate at least a presence or an absence of a test subject compound in a specimen may be summarized as including: receiving, by one or more computing devices, a set of image information that represents an image of each of the plurality of testing areas, each testing area represented by a respective plurality of pixels in the set of image information; and for each of the testing areas determining, by the one or more computing devices, a number of pixels that indicate as positive for the presence of the test subject compound; for each of the testing areas determining, by one or more computing devices, if the number of pixels that indicate as positive equals or exceeds a first minimum threshold value which indicates that the testing area is positive for the presence of the test subject compound; determining, by the one or more computing devices, a number of testing areas that indicate positive for the presence of the test subject compound; and determining, by the one or more computing devices, if the number of testing areas that indicate positive for the presence of the test subject compound equals or exceeds a second minimum threshold value which indicates an overall positive test result for the presence of the test subject compound.

The computer-implemented method may further include outputting the overall test result using at least one output device. The computer-implemented method may further include determining, by the one or more computing devices, the positive indication of the plurality of pixels for the presence of the test subject compound by assessing the intensity of a colorimetric change of the pixels. Assessing, by the one or more computing devices, the intensity of a colorimetric change may include assessing criteria taken from the group consisting of hue, saturation and brightness or any combination thereof. The computer-implemented method may further include: assessing, by the one or more computing devices, the presence or the absence of the test subject compound based upon a colorimetric test. Assessing the presence or absence of the test subject compound in the colorimetric test may include assessing a Guaiac test. Assessing the presence or absence of the test subject compound may include assessing, by the one or more computing devices, the presence or absence of hemoglobin. The computer-implemented method may further include determining, by the one or more computing devices, the number of pixels within each testing area as indicating positive in the presence of the hemoglobin. The computer-implemented method may further include determining, by the one or more computing devices, the number of pixels within each testing area that turn blue in the presence of the hemoglobin. Determining, by the one or more computing devices, the number of testing areas indicating the presence or absence of the subject test compound may include determining, by the one or more computing devices, the presence or absence of the subject test compound in six testing areas. Determining, by the one or more computing devices, the overall positive test result for the presence of the subject test compound may include determining, by the one or more computing devices, that five of the six testing areas are indicated as positive for the presence of the subject test compound. Determining, by the one or more computing devices, the overall positive test result for the presence of the subject test compound may include determining, by the one or more computing devices, that all of the testing areas are indicated as positive for the presence of the subject test compound. The computer-implemented method may further include determining the validity of the specimen, by the one or more computing devices, by assessing an optical specimen validity marker, the color of which indicates the validity of the specimen. Determining the validity of the specimen, by the one or more computing devices, may include assessing a received image of the optical specimen validity marker and determining the validity of the specimen based upon the color of the pixels in the image. Assessing the presence or absence of a test subject compound, by the one or more computing devices, may minimize the number of false-positive overall test results.

A specimen analysis system to analyze specimen test articles that include a plurality of testing areas that indicate at least a presence or an absence of a test subject compound in a specimen may be summarized as including at least one processor; and at least one non-transitory processor-readable medium that is communicatively coupled to the at least one processor and that stores at least one of processor-executable instructions or data that, when executed by the at least one processor, cause the at least one processor to: receive a set of image information that represents an image of each of the plurality of testing areas, each of the testing areas represented by a respective plurality of pixels in the set of image information; for each of the plurality of testing areas, determine a number of pixels that indicate as one of either the presence or the absence of the test subject compound; for each of the testing areas, determine if the number of pixels that indicate one of either the presence or the absence of the test subject compound equals or exceeds a first minimum threshold value which indicates that the testing area is positive for one of either the presence or the absence of the test subject compound; determine a number of testing areas that indicate positive for one of either the presence or the absence of the test subject compound; and determine if the number of testing areas that indicate positive for one of either the presence or the absence of the test subject compound equals or exceeds a second minimum threshold value which indicates an overall positive test result for one of either the presence or the absence of the test subject compound.

The specimen analysis system may further include at least one output device that outputs the overall test results. To determine the positive indication of the plurality of pixels for one of either the presence or the absence of the test subject compound the processor may assess the intensity of a colorimetric change of the pixels. To assess the intensity of a colorimetric change the processor may assess criteria taken from the group consisting of hue, saturation and brightness or any combination thereof. The specimen test article may include a colorimetric specimen test. The colorimetric specimen test may be a Guaiac test. The test subject compound may be hemoglobin. The plurality of pixels may be determined to indicate as positive in the presence of the hemoglobin. The plurality of pixels may be blue in the presence of the hemoglobin. The plurality of testing areas may be six. Five of the six testing areas may be respectively determined to indicate as positive for one of either the presence or the absence of the test subject compound to achieve an overall positive test result indicating the presence or the absence of the subject test compound. All of the plurality of testing areas may be determined to indicate as positive for one of either the presence or the absence of the test subject compound to achieve an overall positive test result indicating the presence or the absence of the subject test compound. A number of false-positive overall test results may be minimized.

The specimen test article may further include an optical specimen validity marker, the color of which indicates the validity of the specimen. The processor may receive an image of the optical specimen validity marker and determines the validity of the specimen based upon the color of the pixels in the image.

A computer-implemented method to analyze specimen test articles that include a plurality of testing areas that indicate at least a presence or an absence of a test subject compound in a specimen may be summarized as including receiving, by one or more computing devices, a set of image information that represents an image of each of the plurality of testing areas, each testing area represented by a respective plurality of pixels in the set of image information; and for each of the testing areas determining, by the one or more computing devices, a number of pixels that indicate as one of either the presence or the absence of the test subject compound; for each of the testing areas determining, by one or more computing devices, if the number of pixels that indicate as one of either the presence or the absence of the test subject compound equals or exceeds a first minimum threshold value which indicates that the testing area is positive for one of either the presence or the absence of the test subject compound; determining, by the one or more computing devices, a number of testing areas that indicate positive for one of either the presence or the absence of the test subject compound; and determining, by the one or more computing devices, if the number of testing areas that indicate positive for one of either the presence or the absence of the test subject compound equals or exceeds a second minimum threshold value which indicates an overall positive test result for one of either the presence or the absence of the test subject compound.

The computer-implemented method may further include outputting the overall test result using at least one output device.

The computer-implemented method may further include determining, by the one or more computing devices, the positive indication of the plurality of pixels for one of either the presence or the absence of the test subject compound by assessing the intensity of a colorimetric change of the pixels. Assessing, by the one or more computing devices, the intensity of a colorimetric change may include assessing criteria taken from the group consisting of hue, saturation and brightness or any combination thereof.

The computer-implemented method may further include assessing, by the one or more computing devices, the presence or the absence of the test subject compound based upon a colorimetric test. Assessing the presence or absence of the test subject compound in the colorimetric test may include assessing a Guaiac test. Assessing the presence or absence of the test subject compound may include assessing, by the one or more computing devices, the presence or the absence of hemoglobin.

The computer-implemented method may further include determining, by the one or more computing devices, the number of pixels within each testing area as indicating positive in one of either the presence or the absence of the hemoglobin.

The computer-implemented method may further include determining, by the one or more computing devices, the number of pixels within each testing area that turn blue in the presence of the hemoglobin. Determining, by the one or more computing devices, the number of testing areas indicating one of either the presence or the absence of the subject test compound may include determining, by the one or more computing devices, the presence or the absence of the subject test compound in six testing areas. Determining, by the one or more computing devices, the overall positive test result for one of either the presence or the absence of the subject test compound may include determining, by the one or more computing devices, that five of the six testing areas are indicated as positive for one of either the presence or the absence of the subject test compound. Determining, by the one or more computing devices, the overall positive test result for one of either the presence or the absence of the subject test compound may include determining, by the one or more computing devices, that all of the testing areas are indicated as positive for either the presence or the absence of the subject test compound.

The computer-implemented method may further include determining the validity of the specimen, by the one or more computing devices, by assessing an optical specimen validity marker, the color of which indicates the validity of the specimen. Determining the validity of the specimen, by the one or more computing devices, may include assessing a received image of the optical specimen validity marker and determining the validity of the specimen based upon the color of the pixels in the image. Assessing the presence or absence of a test subject compound, by the one or more computing devices, may minimize the number of false-positive overall test results.

BRIEF DESCRIPTION OF THE SEVERAL VIEWS OF THE DRAWINGS

In the drawings, identical reference numbers identify similar elements or acts. The sizes and relative positions of elements in the drawings are not necessarily drawn to scale. For example, the shapes of various elements and angles are not necessarily drawn to scale, and some of these elements may be arbitrarily enlarged and positioned to improve drawing legibility. Further, the particular shapes of the elements as drawn, are not necessarily intended to convey any information regarding the actual shape of the particular elements, and may have been solely selected for ease of recognition in the drawings.

FIG. 4 is an example lookup table, according to at least one illustrated embodiment.

FIG. 5 is an example lookup table, according to at least one illustrated embodiment, according to at least one illustrated embodiment.

DETAILED DESCRIPTION

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures and methods (e.g., various components of computing devices, principles of operation of a lateral flow strip, etc.) have not been shown or described in detail to avoid unnecessarily obscuring descriptions of the embodiments.

Unless the context requires otherwise, throughout the specification and claims that follow, the word "comprising" is synonymous with "including," and is inclusive or open-ended (i.e., does not exclude additional, unrecited elements or method acts).

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the context clearly dictates otherwise. It should also be noted that the term "or" is generally employed in its broadest sense, that is, as meaning "and/or" unless the context clearly dictates otherwise.

The headings and Abstract of the Disclosure provided herein are for convenience only and do not interpret the scope or meaning of the embodiments.

Figure 1:
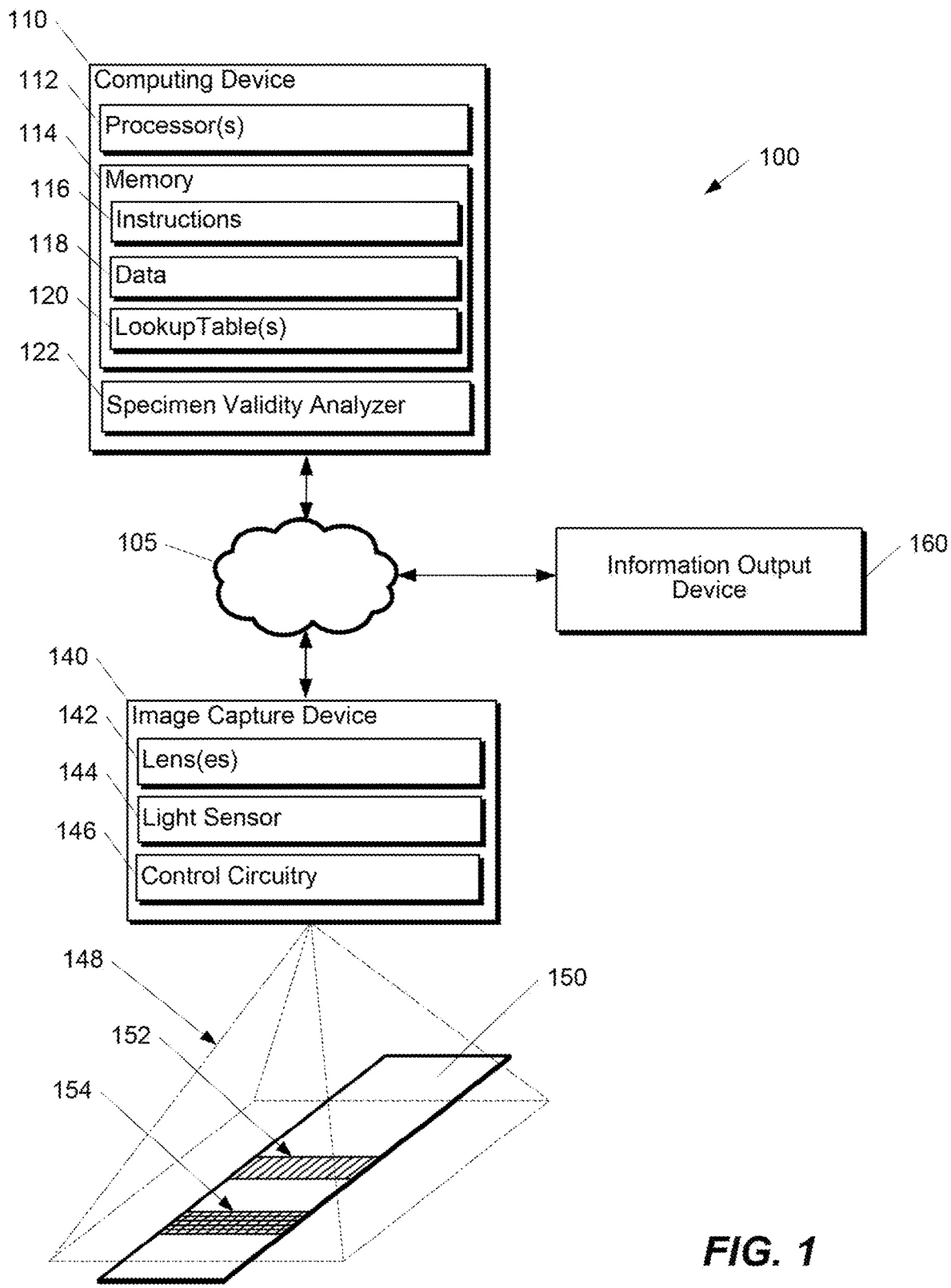
FIG. 1 is a block diagram of an example specimen analysis system, according to at least one illustrated embodiment.

FIG. 1 is block diagram of an example specimen analysis system 100, according to at least one illustrated embodiment. The system 100 includes a computing device 110, an image capture device 140, and an information output device 160 communicatively coupled directly or over a network 105. The system 100 analyzes specimen test articles, such as a specimen test article 150 shown in FIG. 1. In some implementations, a single housing or assembly encloses the computing device 110, the image capture device 140, and information output device 160.

The specimen test article 150 is used to test for the presence or absence of a test subject substance in a specimen. As examples, the specimen test article 150 can test a specimen for the presence or absence of alcohol, cocaine, marijuana (THC), amphetamines, performance enhancing drugs, other banned substances, other test subject substances indicative of use of a particular substance, or combinations and/or derivatives thereof. As examples, the specimen can take the form of human or animal urine, blood, saliva, semen, or other bodily fluids or bodily matter.

The specimen test article 150 includes at least one optical test substance marker 152. The optical test substance marker 152 indicates at least the presence or the absence of the test subject substance in the specimen. For example, a color of the optical test substance marker 152 indicates the presence or absence of the test subject substance in the specimen. As one example, the color of the optical test substance marker 152 remains unchanged from a first color if the specimen does not contain the test subject substance, while the color of the optical test substance marker 152 changes from the first color to a second, different color if the test subject substance is present within the specimen.

In some implementations, presence of the test subject substance within the specimen may be defined as an amount or concentration of the test substance that is greater than a threshold value. Furthermore, in some implementations, the color of the optical test substance marker 152 changes along a spectrum or among a plurality of colors to indicate an amount or a concentration of the test subject substance within the specimen.

The specimen test article 150 also includes at least one optical specimen validity marker 154 in addition to the optical test substance marker 152. In some implementations, the optical specimen validity marker 154 is spaced from the optical test substance marker 152 (e.g., such that the two markers 154 and 152 are readily distinguishable from each other).

A color of the optical specimen validity marker 154 indicates a validity of the specimen. Thus, in contrast to the test subject substance for which the specimen is principally being tested, the specimen validity maker 154 provides an indication of whether or not the specimen itself is valid or authentic, and/or unadulterated or untampered. As an example, where the optical test substance maker 152 may indicate the presence or absence of cocaine within the specimen, the specimen validity maker 154 may indicate whether the specimen itself is human urine.

As one example method of operation, the optical specimen validity marker 154 changes colors in the presence of an adulterant, where the presence of an adulterant renders the specimen invalid. As another example, the optical specimen validity marker 154 may remain the same color in the absence of a particular substance in the specimen, where the absence of the particular substance in the specimen renders the specimen invalid.

As yet another example, the color of the optical specimen validity marker 154 may indicate a value or status of a physical characteristic of the specimen. The validity of the specimen is then inferable or otherwise determinable from the indicated value or status of the physical characteristic. As examples, the physical characteristic can include a pH of the specimen, a specific gravity of the specimen, a salinity of the specimen, a temperature of the specimen, or other physical characteristics or combinations of characteristics.

Thus, the optical specimen validity marker 154 may assess specimen validity according to many different methods of operation, including detection of an adulterant within the specimen, absence of a substance expected to be found in unadulterated specimens, specimen physical characteristics, or other techniques or combinations thereof.

As one example, if the optical specimen validity marker 154 indicates that the temperature of a specimen (e.g., human urine specimen) is less than a threshold temperature, the specimen may be ruled invalid. Such may advantageously detect submission by the donor of a specimen not produced within a designated testing area or testing period.

As a further example, the optical specimen validity marker 154 may test for the presence of acidic and/or alkaline adulterants within a human urine specimen. In particular, the color of the optical specimen validity marker 154 may indicate a pH of the specimen. Human urine typically has pH values that range from 4.0 to 9.0. Therefore, if the color of specimen validity marker 154 indicates that the specimen has a pH below 4.0 or above 9.0, the specimen may be ruled invalid.

As another example, the optical specimen validity marker 154 may test for dilution of a human urine specimen. In particular, the color of the optical specimen validity marker 154 may indicate a specific gravity of the specimen. Human urine typically has specific gravity values that range from 1.003 to 1.030. Therefore, if the color of specimen validity marker 154 indicates that the specimen has a specific gravity below 1.003 or above 1.030, the specimen may be ruled invalid.

As another example, the optical specimen validity marker 154 may test for the presence of oxidants, such as bleach or peroxide, within a human urine specimen. In particular, the optical specimen validity marker 154 may turn a blue or green color in the presence of oxidants. Therefore, if the specimen validity marker 154 is the blue or green color, the specimen may be ruled invalid.

As another example, the optical specimen validity marker 154 may test for dilution of a human urine specimen by indicating the presence or absence of creatinine, which is a waste product of creatine and is typically present in human urine. In particular, the color of the optical specimen validity marker 154 may indicate the presence or absence of creatinine. For example, a donor may attempt to alter a test by consuming excessive amounts of water or diuretics to "flush" his or her urinary system. Therefore, if the color of the specimen validity marker 154 indicates an absence of creatinine within the specimen (e.g., less than 5 mg/dl), the specimen may be ruled invalid.

As another example, the color of the optical specimen validity marker 154 may indicate the presence or absence of nitrites a human urine specimen. In particular, nitrites are contained within many commercially available urine adulterants and work by oxidizing a major cannabinoid metabolite THC-COOH. Unadulterated urine does not normally contain any nitrites. Therefore, if the color of the specimen validity maker 154 indicates the presence of nitrites within the specimen, the specimen may be ruled invalid.

As yet another example, the color of the optical specimen validity maker 154 may indicate the presence of one or more aldehydes such as glutaraldehyde within a human urine specimen. In particular, glutaraldehyde is contained within many commercially available urine adulterants and causes false negative screening results by disrupting an enzyme used in some specimen test articles 150. Unadulterated urine does not normally contain any aldehydes. Therefore, if the color of the specimen validity maker 154 indicates the presence of aldehydes within the specimen, the specimen may be ruled invalid.

In some implementations, presence or absence of a particular substance (e.g., an adulterant) within the specimen may be defined as an amount or concentration of the substance that is greater than or less than a threshold value. Furthermore, in some implementations, the color of the optical specimen validity maker 154 changes along a spectrum or among a plurality of colors to indicate an amount or a concentration of a particular substance within the specimen or to indicate a range of potential values of a physical characteristic of the specimen. For example, the optical specimen validity marker 154 may increasingly change from a first color to a second color to indicate the pH of the specimen within a range of potential pH values or may increasingly change from the first color to the second color to indicate a concentration of, for example, aldehydes within the specimen.

In some implementations, the specimen test article 150 includes two or more specimen validity markers 154 which operate to assess specimen validity according to different methods. In some of such implementations, if any of the two or more markers 154 indicate that the specimen is invalid, then the specimen may be ruled invalid. In others of such implementations, if greater than or equal to some predetermined number of the two or more markers 154 (e.g., two, three, all, etc.) indicate that the specimen is invalid, then the specimen may be ruled invalid.

In some implementations, the specimen test article 150 additionally includes a control marker (not shown) that simply indicates whether the specimen test article properly absorbed or otherwise received the specimen. Further, in some implementations, the specimen test article 150 includes only the optical specimen validity marker 154 and not the optical test substance marker 152. In some implementations, the specimen test article 150 is a lateral flow strip.

In addition, although certain of the example test subject substances discussed above are illicit or banned substances, the present disclosure is not limited to testing for such category of substances. Instead, the systems and methods of the present disclosure can be used with any specimen test article 150 that includes an optical specimen validity marker 154 that indicates with its color a validity characteristic of the specimen. As an example, the specimen analysis system 100 can be used to assess a validity characteristic of a specimen that is tested for one or more substances indicative of various illnesses, diseases, genetic traits, or other medically pertinent information. Therefore, the specimen analysis system 100 may be used in conjunction with or as a portion of a diagnostic protocol. For example, the specimen test article 150 may be a diagnostic assay.

The image capture device 140 can be any device capable of capturing an image. For example, the image capture device 140 can be one or more of many different types of cameras, scanners, or other devices capable of capturing an image or image data.

As an example, the image capture device 140 includes a number of lenses 142 that modify, redirect, and/or focus light entering the image capture device 140 through an aperture. A light sensor 144 receives the light that passes through the lenses 142 and outputs data representative of a plurality of pixels of an image. For example, the light sensor 144 can output data representative of a color for each of the plurality of pixels, as discussed further below.

The image capture device 140 also includes control circuitry 146 that controls operation of the image capture device 140. For example, the control circuitry 146 controls image capture timing, image capture rate, image resolution, or other parameters of image capture device 140. In some implementations, the computing device 110 controls or provides instructions to the image capture device 140 directly or via network 105.

The image capture device 140 captures an image of a field of view 148 of the image capture device 140. As shown in FIG. 1, the specimen test article 150 is positioned relative to the image capture device 140 such that at least a specimen validity portion of the specimen test article which includes the at least one optical specimen validity marker 154 is included within the field of view 148 and corresponding captured image. The at least one optical test substance marker 152 may be included within the field of view 148 and corresponding captured image, as shown in FIG. 1, or may not be included within the field of view 148 and corresponding captured image.

In some implementations, the image capture device 140 includes a structure or device that receives the specimen test article 150 and positions the specimen validity portion of the test article 150 within the field of view 148. As one example, a cartridge that is insertable into the image capture device 140 or an associated structure receives and holds the specimen test article 150. Alternatively or additionally, system 100 may include other means for placing the specimen test article 150 in a known position and/or orientation relative to the image capture device 140. Such may advantageously allow the captured image to depict only the optical specimen validity marker 154 or otherwise allow simplified identification and/or isolation of the pixels of the captured image that corresponds to the optical specimen validity marker 154.

In further implementations, the image capture device includes one or more internal or external light sources to illuminate the specimen test article 150 during image capture. For example, the light source(s) can include one or more light emitting diodes, lamps, incandescent bulbs, infrared light sources, light sources for inducing fluorescence from the article 150 (e.g., from marker 152 and/or marker 154), or other light sources.

The image capture device 140 outputs or otherwise provides to the computing device 110 directly or over network 105 a set of image information that represents the captured image of at least the specimen validity portion of the specimen test article 150. For example, the set of image information includes data representative of a plurality of pixels of the image. In particular, the data includes three or more color component values for each of the plurality of pixels. Each of the color component values is representative of an amount of a respective color component of a color of the corresponding pixel.

As one example, the color component values for each pixel include a red color component value, a green color component value, and a blue color component value, thereby describing the color of such pixel within the RGB color space. For example, each of such values may range from 0 to 255. However, other color component value ranges may be used.

In other implementations, alternatively or in addition to the RGB color space, the color component values included in the set of image information can describe colors of pixels according to the RGBA color space, CMYK color space, YIQ color space, YPbPr color space, xvYCC color space, HSV color space, HSL color space, or other color spaces or color models, or combinations thereof. The computing device 110 uses the color component values to assess the optical specimen validity maker 154, as discussed further below.

The computing device 110 can be an embedded computing device, a desktop computer, a laptop computer, a tablet computer, a smartphone, one or more server computing devices, or some combination thereof. The computing device 110 can perform computing operations according to any computer architecture, including parallel, sequential, and/or distributed computing architectures.

Computing device 110 includes a processor 112 and a memory 114. The processor 112 can be one processor or a plurality of processors that are operatively coupled. The processor 112 can be any processing device, such as a microprocessor, microcontroller, integrated circuit, circuitry that implements computer logic, or some combination thereof.

The memory 114 can include any non-transitory information storage device, including, but not limited to, RAM, ROM, hard drives, flash drives, optical media, other memory devices, or some combination thereof. The memory 114 can store information accessible by processor 112, including instructions 116 that can be executed by processor 112. The instructions 116 can be any set of instructions that when executed by the processor 112, cause the processor 112 to provide desired functionality. The memory 114 can also store data 118.

The computing device 110 includes a specimen validity analyzer 122. The computing device 110 implements the specimen validity analyzer 122 to assess at least one specimen validity characteristic of the specimen. In some implementations, the specimen validity analyzer 122 assesses the at least one specimen validity characteristic based at least in part on a set of color component values determined for one or more pixels of the image of the specimen test article 150. For example, computing device 110 can implement specimen validity analyzer 122 to perform aspects of methods 200 and 300 of FIGS. 2 and 3, respectively, as discussed further below.

In some implementations, the specimen validity analyzer 122 includes processor-executable instructions 116 stored in or loaded into memory 114 and executed by processor 112. In other implementations, the specimen validity analyzer 122 includes one or more circuits (e.g., integrated circuits), logic components, or other items of computer hardware arranged to implement computer logic or perform other functionality. In other implementations, the specimen validity analyzer 122 can be implemented using some combination of processor-executable instructions 116 or data 118 and circuitry.

In some implementations, the memory 114 also stores one or more lookup tables 120. Each lookup table 120 stores information usable in association with one or more particular varieties of specimen test articles 150. For example, each different variety of specimen test article 150 may test for a different test substance or may test specimen validity according to a different respective methods of operation.

The lookup table 120 for each particular variety of specimen test article 150 provides a mapping of potential colors of specimen validity marker 154 to particular respective test results indicated by such colors. More precisely, the lookup table for each particular variety of specimen test article 150 logically associates each of a plurality of sets of reference color component values with a particular result or value of at least one specimen validity characteristic. The same or additional lookup tables can provide analogous information for marker 152.

As an example, FIG. 4 is an example lookup table 400, according to at least one illustrated embodiment. Lookup table 400 includes a plurality of sets of reference color component values in a first column 402 and a plurality of specimen validity characteristic results or values in a second column 404. Each set of reference color component values (e.g., sets 410, 412, and 414) is respectively logically associated with a particular specimen validity characteristic result (e.g., validity characteristic results 420, 422, and 424).

Referring again to FIG. 1, in some implementations, the lookup table 120 for a particular specimen test article 150 logically associates each set of reference color component values with a particular value of a physical characteristic of the specimen. In some implementations, the lookup table 120 further logically associates each set of reference color component values and/or each particular value of the physical characteristic with a particular specimen validity status.

As an example, FIG. 5 is an example lookup table 500, according to at least one illustrated embodiment. Lookup table 500 includes a plurality of sets of reference color component values in a first column 502; a plurality of specimen physical characteristic values in a second column 504; and a plurality of specimen validity status results or values in a third column 506. Each set of reference color component values (e.g., sets 510, 512, 514, and 516) is respectively logically associated with a particular specimen physical characteristic value (e.g., physical characteristic values 520, 522, 524, and 526). Furthermore, each set of reference color component values and/or each physical characteristic value is respectively logically associated with a particular specimen validity status (e.g., statuses 530, 532, 534, and 536).

Referring again to FIG. 1, in some implementations, the specimen validity analyzer 122 uses the lookup tables 120 to assess at least one specimen validity characteristic of the specimen. For example, the specimen validity analyzer 122 may use the lookup tables 120 to map a set of color component values representative of a color of the specimen validity marker 154 to a particular specimen validity characteristic outcome, as discussed further below with respect to methods 200 and 300 of FIGS. 2 and 3, respectively.

Generally, the information stored within each lookup table 120 (e.g., sets of reference color component values, specimen validity characteristic values, physical characteristic values, and/or specimen validity statuses) and their associated relationships are predetermined through testing or calibration of the corresponding variety of specimen test article 150 with reference specimen samples having known validity or physical characteristic values.

As one example, a particular variety of specimen test articles 150 may test for the presence of acidic and/or alkaline adulterants within human urine by indicating specimen pH, as discussed above. The pH values of unadulterated human urine typically range from 4.0 to 9.0. Therefore, pH values below 4.0 or above 9.0 for a specimen are indicative of adulteration. As such, to generate the lookup table 120 for such particular variety of specimen test articles 150, reference specimen samples having known pH values may be respectively placed on different specimen test articles 150 of such variety. The resulting color of the optical specimen validity marker 154 of each respective specimen test article 150 may be determined (e.g., in the form of sets of reference color component values) and logically associated with the known pH of the reference specimen sample to which such test article 150 was subjected.

In some implementations, an operator of the system 100 performs such example calibration or testing process to obtain the information and relationships stored in the lookup tables 120. In other implementations, a manufacturer of a particular variety of specimen test articles 150 provides the lookup table 120 or the information stored within the lookup table 120 (e.g., in the form of a computer-readable file or in the form of a textual description that an operator of the system 100 inputs into the computing device 110).

Furthermore, the respective structures of the example lookup tables 400 and 500 of FIGS. 4 and 5 are provided as examples only. Lookup tables 120 may have other, different structures, as well.

The particular reference color component values or physical characteristic values contained within a lookup table 120 may be spaced along uniform intervals or may be spaced along non-uniform intervals. For example, in some implementations, the reference color component values or physical characteristic values included in a lookup table 120 may be particularly grouped around values that correspond to transitions between valid and invalid specimens. To continue the example provided above, a lookup table 120 for specimen test articles 150 that test for the presence of acidic and/or alkaline adulterants within human urine via specimen pH value may include relatively greater numbers of sets of reference color component that respectively correspond to pH values grouped around pH 4.0 and pH 9.0, thereby providing increased testing granularity around the transitions between valid and invalid human urine specimens.

System 100 further includes the information output device 160. The information output device 160 provides information regarding at least specimen validity characteristic of the specimen that has been assessed by the system 100 to a user. For example, the information output device 160 can be any display device to present or show the information, including, for example, a monitor, a screen, a holographic display, a projection display, a three-dimensional display, etc.

As another example, the information output device 160 can include a plurality of light emitting diodes, with each of the light emitting diodes corresponding to a different value or outcome of the at least one specimen validity characteristic. The system 100 can illuminate one or more light emitting diodes to convey information regarding the assessed specimen validity characteristic.

As yet another example, the information output device 160 can include a printer to print information, a speaker to audibly output information, and/or a network interface to transmit information regarding the assessed specimen validity characteristic to one or more remote devices or systems via network 105.

Network 105 can be any type of communications network, such as a local area network (e.g., intranet), a wide area network (e.g., Internet), or some combination thereof and can include any number of wired or wireless links. In general, communication between the components of system 100 via network 105 can be carried via any type of wired and/or wireless connection, using a wide variety of communication protocols (e.g., TCP/IP, HTTP, SMTP, FTP), encodings or formats (e.g., HTML, XML), and/or protection schemes (e.g., VPN, secure HTTP, SSL). Thus, communications over network 105 can include direct, wired communication, wireless communications, or combinations thereof. For example, network 105 can include a direct, wired communicative connection (e.g., wired USB connection) between computing device 110 and image capture device 140.

Figure 2:
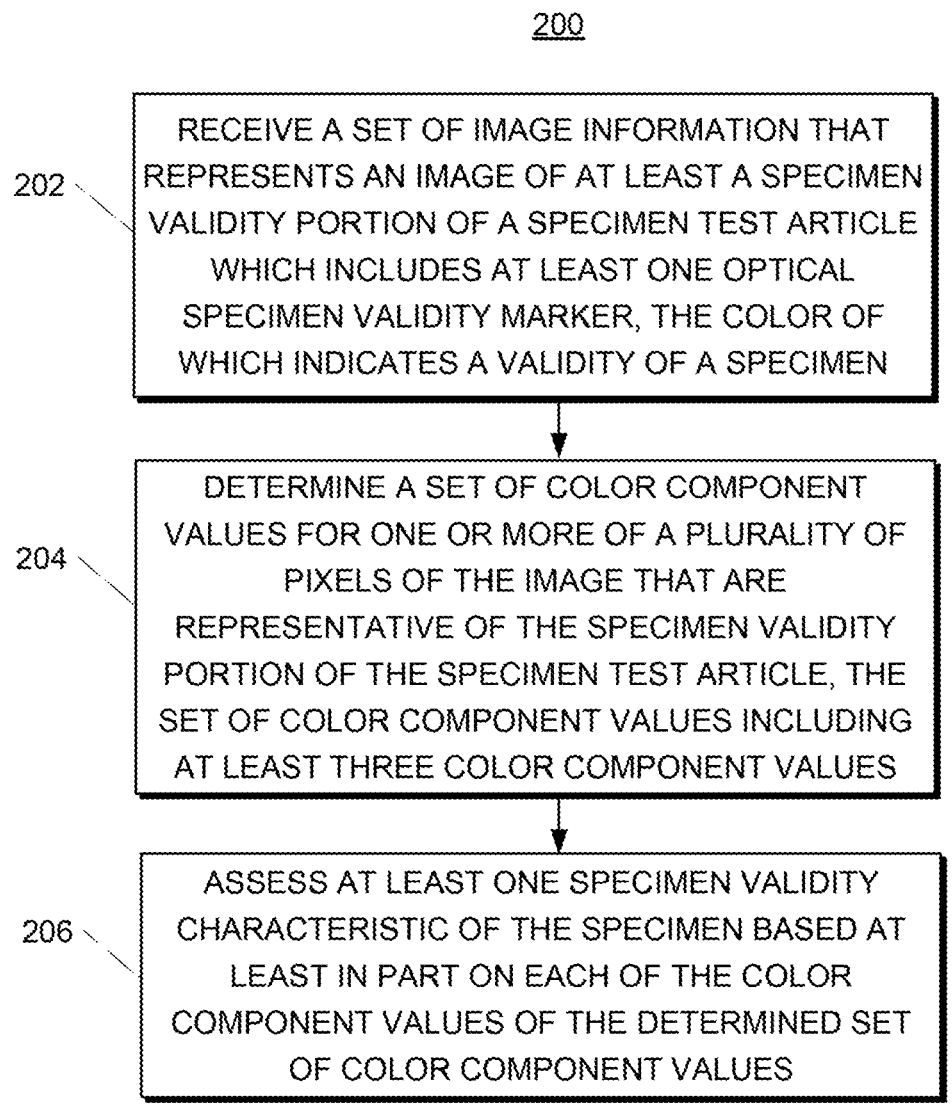
FIG. 2 is a flow chart diagram showing an example method to analyze specimen test articles, according to at least one illustrated embodiment.

FIG. 2 is a flow chart diagram showing an example method 200 to analyze specimen test articles, according to at least one illustrated embodiment. Although method 200 is discussed herein with reference to the specimen validity analyzer 122 of FIG. 1, any suitable specimen analysis system can perform method 200. Likewise, certain portions of method 200 may be performed by other components of system 100 alternatively or in addition to the specimen validity analyzer 122. Method 200 begins at 202.

At 202, the specimen validity analyzer 122 receives a set of image information that represents an image of at least a specimen validity portion of a specimen test article. The specimen validity portion of the test article includes the at least one optical specimen validity marker, the color of which indicates a validity of the specimen. For example, the specimen validity analyzer 122 can receive a set of image information from the image capture device 140 that represents a captured image of the specimen test article 150 which includes the optical specimen validity marker 154.

In some implementations, the set of image information describes a plurality of pixels of the image. In particular, the set of image information can include, for each of the plurality of pixels, at least three color component values that describe the color of such pixel. Each of the color component values can represent an amount of a color component of the color of the corresponding pixel. For example, the color component values can describe colors according to according the RGB color space, RGBA color space, CMYK color space, YIQ color space, YPbPr color space, xvYCC color space, HSV color space, HSL color space, or other color spaces or color models, or combinations thereof.

At 204, the specimen validity analyzer 122 determines a set of color component values for one or more of a plurality of pixels of the image that are representative of the specimen validity portion of the specimen test article. The set of color component values includes at least three color component values.

In some implementations, the specimen validity analyzer 122 determines the set of color component values at 204 by performing one or more preprocessing routines or operations to isolate or otherwise identify the image data that corresponds to pixels of the captured image that are representative of the optical specimen validity marker 154.

As an example, in some implementations, the specimen test article 150 includes an additional optically identifiable marker or symbol that indicates a known direction, has a known size, and/or has a known position relative to the optical specimen validity marker 154. The specimen validity analyzer 122 identifies the additional symbol; computes or otherwise determines the location and size of the optical specimen validity marker 154 within the image based on the size, direction, and/or position of the additional symbol; and isolates or otherwise identifies the image data that corresponds to pixels of the captured image that are representative of the optical specimen validity marker 154. In some implementations, the additional symbol is included or located within the optical specimen validity marker 154.

As another example, in some implementations, the specimen validity analyzer 122 identifies or determines an outline or perimeter of the specimen test article 150; computes or otherwise determines the location and size of the optical specimen validity marker 154 within the image based on the perimeter of the specimen test article 150; and isolates or otherwise identifies the image data that corresponds to pixels of the captured image that are representative of the optical specimen validity marker 154. In other implementations, the specimen validity analyzer 122 directly identifies an outline or perimeter of the optical specimen validity marker 154. In yet other implementations, the specimen validity analyzer 122 performs other, different preprocessing operations in addition or alternatively to the above described operations.

In some implementations, the specimen validity analyzer 122 determines the set of color component values for the one or more pixels representative of the specimen validity portion of the specimen test article at 204 by calculating a set of average color component values (e.g., mean or median) across all of such pixels. In further implementations, the specimen validity analyzer can identify and disregard pixels having outlying color component values.

Thus, at 204, the specimen validity analyzer determines a set of at least three color component values for one or more pixels representative of the specimen validity portion of the test article 150. For example, the set of determined color component values can include a red color component value, a blue color component value, and a green color component value.

At 206, the specimen validity analyzer 122 assesses at least one specimen validity characteristic of the specimen based at least in part on each of the color component values of the set of color component values determined at 204. As an example, the specimen validity analyzer 122 can assess the validity of the specimen based at least in part on each of the color component values determined at 204. As another example, the specimen validity analyzer 122 can determine a value of a physical characteristic of the specimen based at least in part on each of the color component values determined at 204. In some implementations, the specimen validity analyzer 122 further assesses the validity of the specimen based at least in part on the determined value of the physical characteristic.

Figure 3:
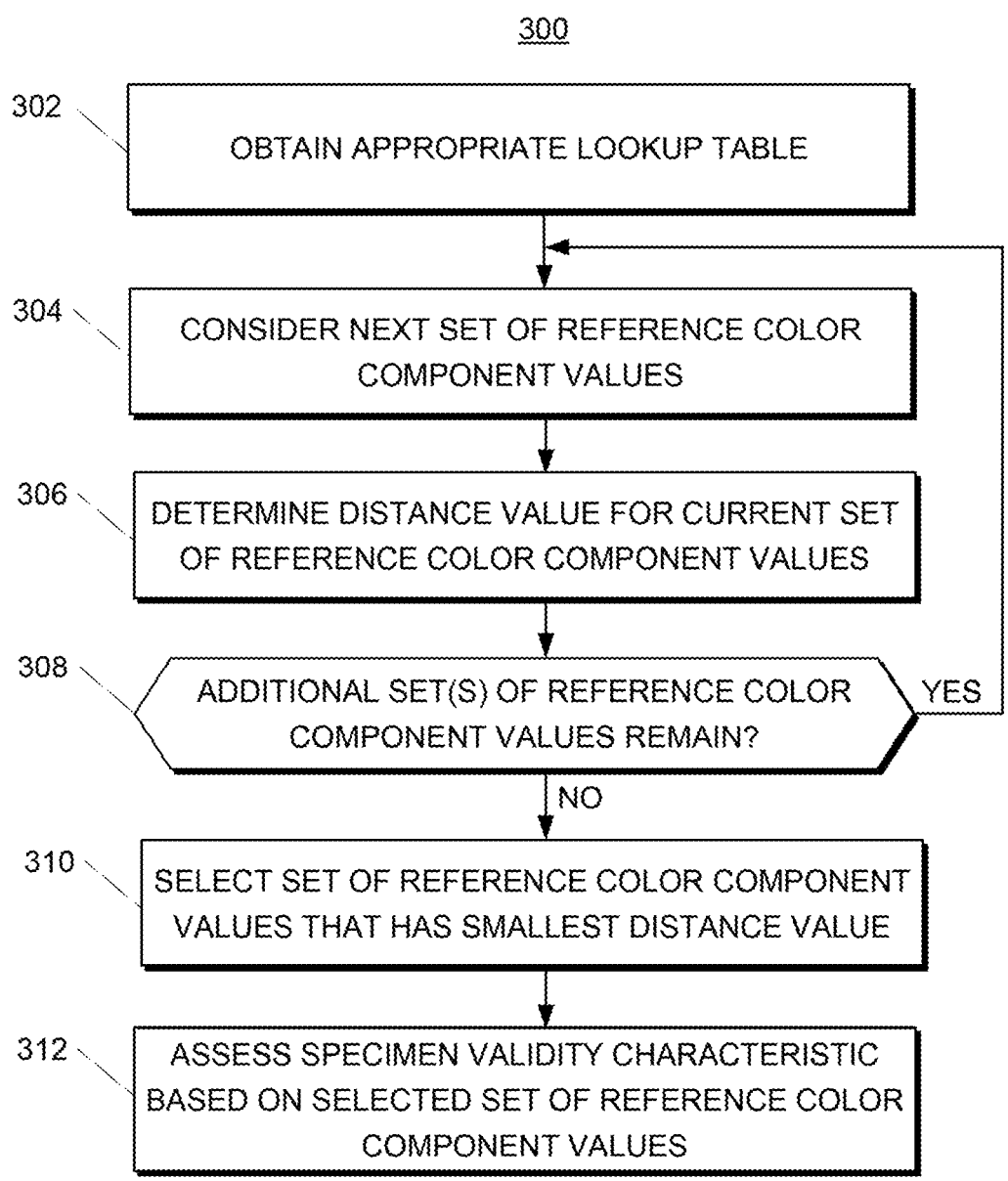
FIG. 3 is a flow chart diagram showing an example method to assess at least one specimen validity characteristic, according to at least one illustrated embodiment.

As one example, FIG. 3 is a flow chart diagram showing an example method 300 to assess at least one specimen validity characteristic, according to at least one illustrated embodiment. Although method 300 is discussed herein with reference to the specimen validity analyzer 122 of FIG. 1, any suitable specimen analysis system can perform method 300. Likewise, certain portions of method 300 may be performed by other components of system 100 alternatively or in addition to the specimen validity analyzer 122. Method 300 begins at 302.

At 302, the specimen validity analyzer 122 obtains an appropriate lookup table. For example, in some implementations, the computing device 110 stores a plurality of lookup tables 120 in memory 114. Each lookup table 120 is associated with a particular variety of specimen test articles 150. For example, a particular variety of specimen test article 150 may test for a particular test substance and/or test and indicate specimen validity according to particular respective methods of operation.

The lookup table 120 associated with each particular variety of specimen test article 150 includes, for example, a set of reference color component values respectively logically associated with a plurality of specimen validity characteristic values or results. Thus, to assess the at least one specimen validity characteristic, the specimen validity analyzer 122 first obtains the particular lookup table 120 that is appropriate for the particular specimen test article 150 being analyzed.

As an example, in some implementations, the specimen test article 150 includes a machine-readable symbol or textual, numeric, or graphical information that identifies the specimen test article 150 or its particular variety. The specimen validity analyzer 122 uses such symbol or information to identify the specimen test article 150 or its particular variety. The specimen validity analyzer 122 then obtains the particular lookup table 120 that is appropriate for the identified variety of specimen test article 150 from memory 114.

In other implementations, the specimen validity analyzer 122 obtains the identity or particular variety of the specimen test article 150 or the identity of the appropriate lookup table 120 via user input.

At 304, the specimen validity analyzer 122 considers the next set of reference color component values. More particularly, the lookup table obtained at 302 includes a plurality of sets of reference color component values. Thus, at 304, the specimen validity analyzer 122 considers the next set of reference color component values. In such fashion, each set of reference color component values is considered individually. Although method 300 shows the specimen validity analyzer considering the sets of reference color component values sequentially, in some implementations, the specimen validity analyzer 122 considers the sets of reference color component values in parallel.

At 306, the specimen validity analyzer 122 determines a distance value for the currently considered set of reference color component values. For example, the specimen validity analyzer 122 inputs the currently considered set of reference color component values into a distance formula to determine the distance value for the current set of reference color component values. The distance formula compares the currently considered set of reference color component values to the set of color component values determined for the one or more pixels to provide the distance value for the current set of reference color component values. In particular, the distance value provided by the distance formula can indicate a "closeness" between the two inputted sets of color component values.

As an example, in some implementations, the specimen validity analyzer 122 uses the following example distance formula to determine the distance value at 306:

$$D = \sqrt{(Test_1 - Ref_1)^2 + (Test_2 - Ref_2)^2 + \ldots + (Test_N - Ref_N)^2} \quad (1)$$

where D is the distance value; $Test_x$ is a member of the set of color component values determined for the one or more pixels representative of the specimen validity portion of the test article; and $Ref_x$ is a member of the currently considered set of reference color component values.

At 308, the specimen validity analyzer 122 determines whether additional sets of reference color component values from the lookup table remain unconsidered. If the specimen validity analyzer 122 determines at 308 that one or more additional sets of reference color component values remain, the specimen validity analyzer 122 returns to 304 and considers the next set of reference color component values.

However, if specimen validity analyzer 122 determines at 308 that no additional sets of reference color component values remain, then specimen validity analyzer 122 proceeds to 310. At 310, the specimen validity analyzer 122 selects the set of reference color component values that has the smallest distance value.

At 312, the specimen validity analyzer 122 assesses at least one specimen validity characteristic based at least in part on the set of reference color component values selected at 310. For example, the specimen validity analyzer 122 may select a specimen validity characteristic value or result that is logically associated with the set of reference color component values selected at 310 in the lookup table obtained at 302.

As another example, the specimen validity analyzer 122 may select a physical characteristic value that is logically associated with the set of reference color component values selected at 310 in the lookup table obtained at 302. In some implementations, at 312, the specimen validity analyzer 122 further selects a specimen validity status that is logically associated with the selected set of reference color component values or the selected physical characteristic value in the obtained lookup table.

In some implementations, after assessing the at least one validity characteristic at 312, the system 100 outputs or provides information regarding the assessed at least one specimen validity characteristic via the information output device 160.

In implementations in which the specimen test article 150 includes two or more optical specimen validity markers 154, the specimen validity analyzer 122 can perform methods 200 and/or 300 with respect to each specimen validity marker 154 sequentially or in parallel.

Furthermore, although the specimen validity analyzer 122 is discussed in reference to method 300 as using a lookup table 120 to select a set of reference color component values and assess the specimen validity characteristic, in some implementation, the specimen validity analyzer 122 uses other data structures to perform such operations, including, for example, various forms of databases, indexes, computations, or other structures.

As an example, in some implementations, the specimen validity analyzer 122 may input a selected set of reference color component values into one or more analytical equations to obtain a physical characteristic value associated with such set of reference color component values. Likewise, in some implementations, the specimen validity analyzer 122 may input a determined physical characteristic value into one or more analytical equations to obtain a specimen validity status or characteristic result associated with such determined physical characteristic value.

In addition, in some implementations, the specimen validity analyzer 122 additionally performs methods similar to methods 200 and 300 of FIGS. 2 and 3 with respect to the optical test substance marker 152 to determine the presence or absence of the test substance within the specimen. For example, the specimen validity analyzer 122 or a different component of computing device 110 can determine a set of color component values for one or more pixels of an image that are representative of the optical test substance marker 152. The specimen validity analyzer 122 or a different component of computing device 110 can assess the presence or absence of a test subject substance within a sample based at least in part on each of the determined color component values. For example, the specimen validity analyzer 122 or a different component of computing device 110 can use a distance formula to compare the determined set of color component values with one or more sets of reference color component values respectively associated with different test subject substance characteristics (e.g., presence or absence). Thus, each of the techniques described above with respect to determination of specimen validity can be analogously applied to determination of the presence of the test subject substance.

In another implementation, the specimen analysis system 100 is used with colorimetric testing devices having colorimetric indicators. In operation, the specimen analysis system 100 determines the level of intensity of a colorimetric change to determine the amount of detected compound found using a colorimetric specimen test article 600 and as indicated by an optical test substance marker 650. Such level of intensity may include determining the hue, saturation and brightness of the pixels in the image captured by the image capture device 140.

Figure 6A:
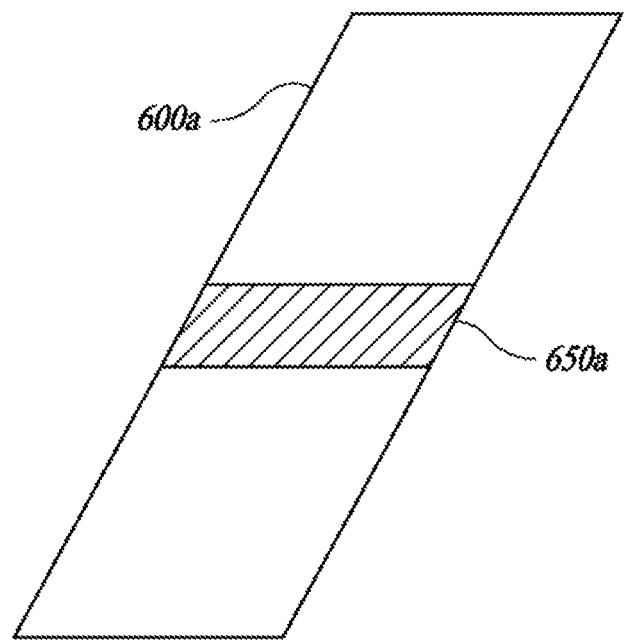
FIG. 6A is an example specimen test article used in colorimetric testing, according to at least one illustrated embodiment.
Figure 6B:
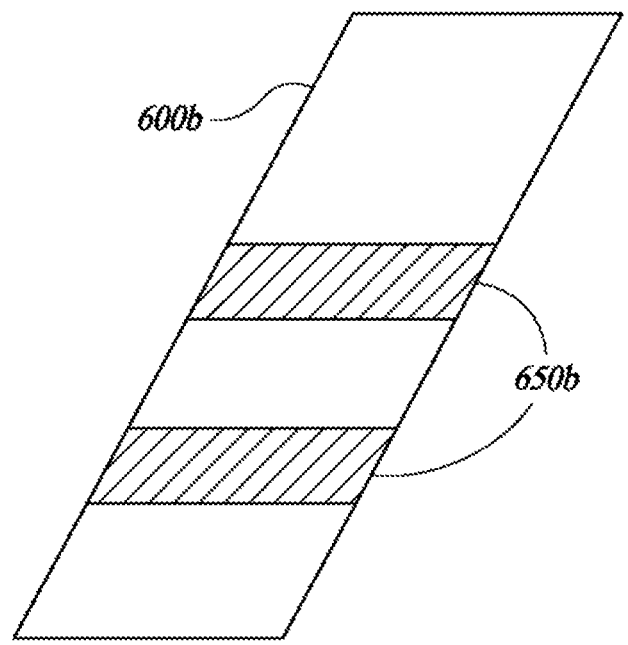
FIG. 6B is another example of a specimen test article used in colorimetric testing.

Generally, colorimetric testing devices use multiple testing areas for analyzing for the presence or non-presence of a test subject compound. As shown in FIG. 6A, the colorimetric specimen test article 600 used with such colorimetric testing devices may include a single optical test substance marker 650, with the marker being divided into multiple testing areas. Alternatively, as shown in FIG. 6B, the colorimetric specimen test article 600 may include multiple optical substance test markers 650, each of which acts as a separate testing area used in the multiple testing area analysis. Alternatively, each of these multiple optical substance test markers 650 may be divided into still further multiple testing areas. As previously discussed, the optical substance test marker(s) 650 can change color in the presence of a detected test substance or compound. In this embodiment, both the color and the intensity of the color can change when a tested substance is present.

Figure 7:
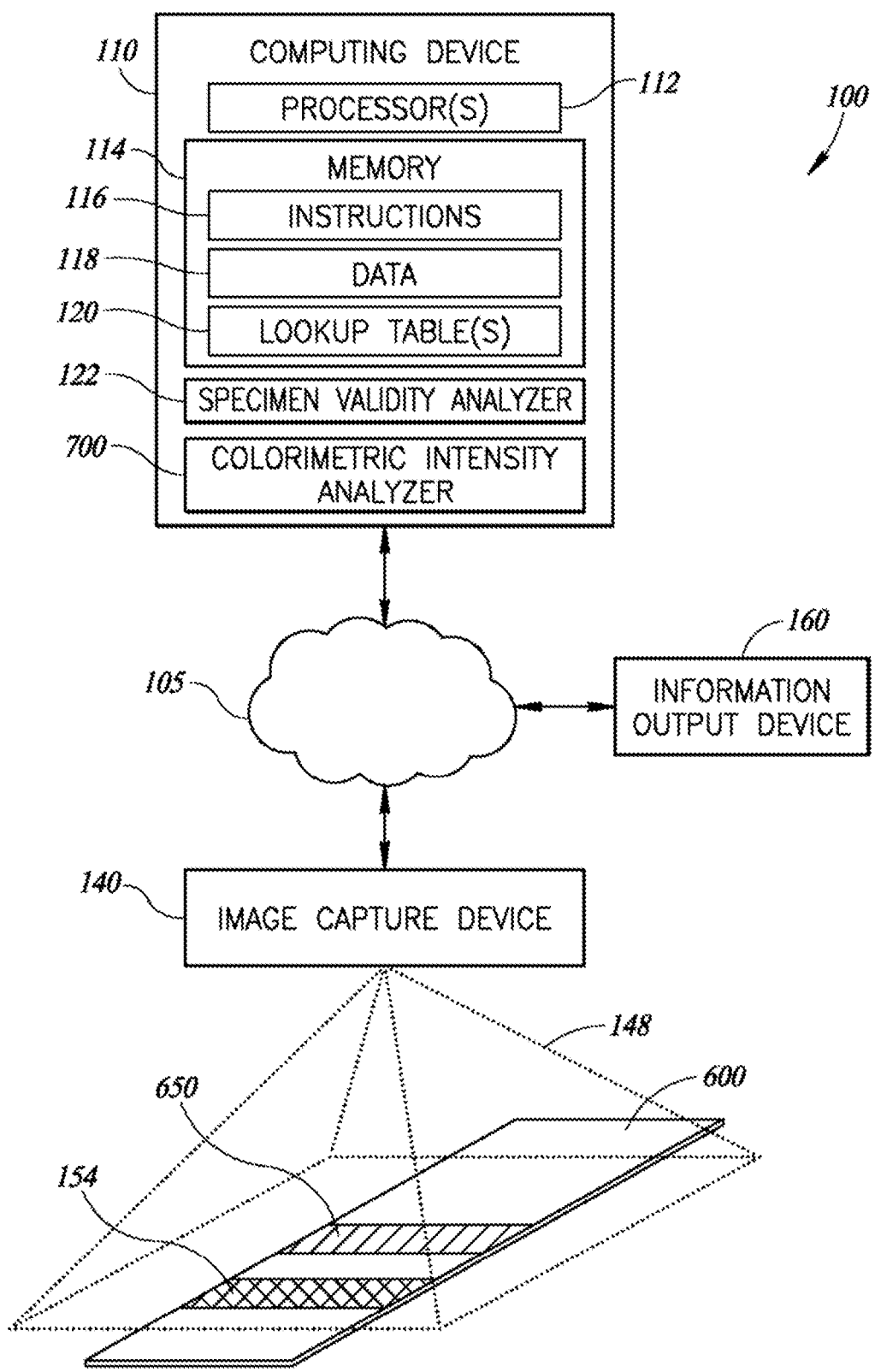
FIG. 7 is a block diagram of an example specimen analysis system used with a colorimetric test, according to at least one illustrated embodiment.

Referring to FIG. 7, a colorimetric intensity analyzer 700 is included in the computing device 110 of specimen analysis system 100. The computing device 110 implements the colorimetric intensity analyzer 700 to assess the color intensity of at least one colorimetric specimen test article 600 (e.g., divided into multiple testing areas) to detect the presence of a test substance or compound. Such color intensity is determined by analyzing the hue, saturation and/or brightness values of the pixels found within each of the plurality of test areas. The image capture device 140 captures an image of the specified testing areas located on colorimetric specimen test article 600 and analyzes the pixels contained in the image. The colorimetric intensity analyzer 700 is used in the specimen analysis system 100 in association with the various devices and components previously discussed above. As such, the functionality and operation of these previously discussed devices and components is not repeated here.

In some implementations, the colorimetric intensity analyzer 700 includes processor-executable instructions 116 stored or loaded into memory 114 and executed by processor 112. In other implementations, the colorimetric intensity analyzer 700 includes one or more circuits (e.g., integrated circuits), logic components, or other items of computer hardware arranged to implement computer logic or perform other functionality. In still other implementations, the colorimetric intensity analyzer 700 can be implemented using a combination of processor-executable instructions 116 and/or data 118 and circuitry.

In operation, the colorimetric intensity analyzer 700 can be set up or programmed for any given colorimetric test and test criteria. By way of example, the size, number and location of the testing areas located on the colorimetric specimen test article 600 can vary with the colorimetric test used. Similarly, the hue, saturation and brightness criteria can be varied to match the indication color of the colorimetric test used. For example, if a Guaiac test for detecting hemoglobin in fecal matter is desired, the parameters for a colorimetric test can be set or programmed to detect and analyze a blue hue having various saturation and brightness criteria. Further, the number of pixels required to indicate a positive or negative result within a specified testing area can also be set or programmed according to the performance criteria of the colorimetric test used. Still further, the number of necessary testing areas showing a positive result and required to indicate an overall positive test condition can be set or programmed to match the colorimetric test's assessment criteria. Finally, the size, number and other criteria may be set or programmed among each of the testing areas themselves allowing multiple different testing areas to be used, if desired. Criteria may, for example, be determined via laboratory studies using known solution concentrations to determine the optimal number of test areas as well as the optimal criteria for each test area. Each test area may have size and/or criteria that are independent from the other test areas. Once determined, this information can be programmed or encoded as one or more parameters for use by the analyzer.

Figure 8:
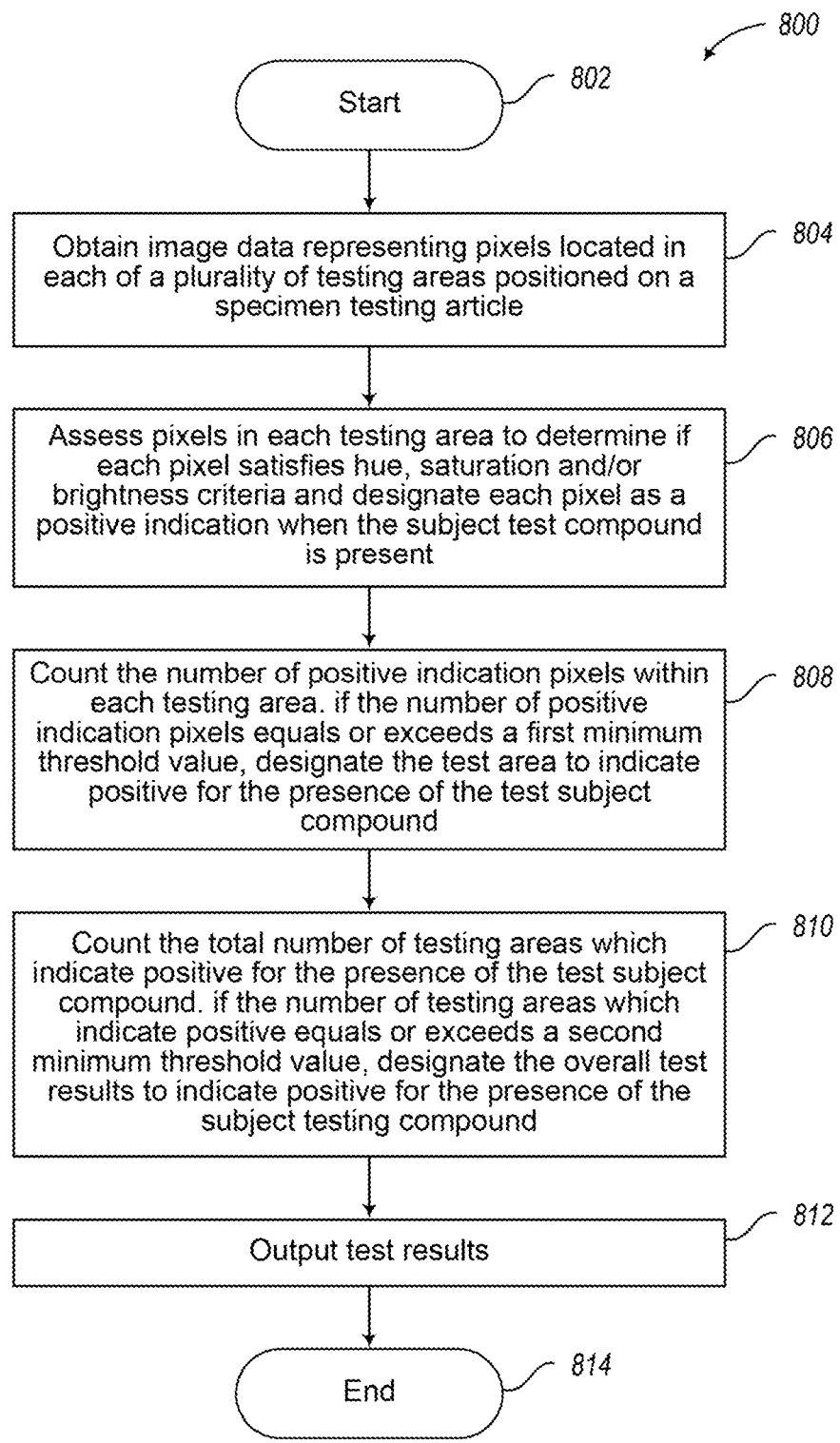
FIG. 8 is a logic flow diagram showing an example method of determining the color intensity of a plurality of pixels in each of a plurality of testing areas, according to at least one illustrated embodiment.

FIG. 8, is a logic flow diagram showing an example method 800 used to analyze the colorimetric specimen test articles 600, in accordance with one illustrated embodiment. Although method 800 is discussed herein with reference to the colorimetric intensity analyzer 700 shown in FIG. 7, any suitable colorimetric intensity analyzer system can perform method 800. Likewise, certain portions of method 800 may be performed by other components of system 100 alternatively or in addition to the colorimetric intensity analyzer 700. Method 800 begins at 801.

At 801, the colorimetric intensity analyzer 700 receives a set of image data that represents an image of the multiple testing areas found in a single optical test substance marker 650 (e.g., the marker divided into multiple testing areas) or each of the multiple optical substance test markers 650 acting as separate testing areas as located on colorimetric specimen test article 600. Generally, the set of image data is captured by image capture device 140. The set of image data includes a plurality of pixels of the image. For each of the plurality of pixels, the set of image data can include the hue, saturation and/or brightness values of each pixel.

At 802, the colorimetric intensity analyzer 700 assesses the pixels within a specified testing area of the one or more optical test substance markers 650 based upon a configured hue, saturation and/or brightness criteria. Each of the criteria for hue, saturation and brightness may be configured and set for a specified colorimetric test. Generally, such criteria for hue, saturation and/or brightness are set as a range of values. If the pixel falls within the desired range for one or more of the hue, saturation and/or brightness values, the colorimetric intensity analyzer 700 determines the pixel as a positive indication (i.e., the presence of the test subject compound or substance has been determined). A range of values for the parameters may, for example, include a hue between 115 and 200, a saturation between 0.1 and 1, a brightness between 0.5 and 1. As previously noted, laboratory studies can be performed using solutions with known concentration values and the results used to generalize and optimize the hue, saturation and brightness ranges. If the pixel falls outside one or more of the value ranges, as configured, the colorimetric intensity analyzer 700 can may ignore the pixel, only identifying positive indicators and ignoring negative indicators, or optionally treat the pixel as a negative indicator (i.e., the non-presence of the test subject compound or substance is determined). Any combination of hue, saturation and brightness values and/or ranges may be used to determine whether a pixel satisfies a positive or negative indication.

At 803, the colorimetric intensity analyzer 700 counts the number of pixels located within each of the multiple testing areas of the one or more optical test substance markers 650 to determine if the number of positive indicating pixels (i.e., satisfying the hue, saturation and/or brightness criteria) is equal to or exceeds a first minimum threshold value used by the colorimetric intensity analyzer 700 for making a positive indication for the presence of the test subject compound in the testing area. This threshold may be dependent on a size of the analysis area. If the analysis area contains thousands of pixels, and the test easily reacts in the presence of the subject compound, then the threshold could, for example, be in the range of hundreds of pixels. Some smaller areas may have a threshold of, for example, only 5 indicated pixels. If the threshold value is met or exceeded, a positive test indication is determined for the testing area. The number of pixels required to satisfy the first minimum threshold value in each testing area can vary based upon the colorimetric test used. Generally, the threshold values are stored in a memory 114 or a lookup table 120 and accessed by the colorimetric intensity analyzer 700 during the testing process.

At 804, the colorimetric intensity analyzer 700 counts the number of testing areas that have been determined as positive indications of the test subject compound's presence. Based upon a second minimum threshold value set and stored in the memory 114 or the lookup table 120 for the colorimetric test in use, the colorimetric intensity analyzer 700 determines if the number of these testing areas is equal to or exceeds the second minimum threshold value of testing areas required to indicate an overall positive test result has been met. For example, in a test with six analysis areas, a threshold could be four, meaning four or more positive or indicated areas designate a positive or indicated result. If so, the test is deemed a positive result indicating the presence of the test subject compound. If not, the test is deemed a negative test result indicating the non-presence of the test subject compound. While generally described in terms of detection of a value that meets at least a minimum threshold value corresponding to a positive result, in some implementations detection of value that at least a minimum threshold value may correspond to an absence of a substance or a negative result. For example, a test may turn GREEN to confirm that a given compound is NOT in the sample, hence the result would be shown as negative. The mapping or relationship between values for various parameters that represent presence or absence of a substance and the corresponding characterization of the results as either positive or negative is configurable, and may for example be user configurable for the colorimetric intensity analyzer 700.

The number of positive indicating testing areas required for an overall positive test result may be specified and configured for any given colorimetric test. For example, one colorimetric test may require two of three specified testing areas to indicate as positive before a positive overall test result is indicated. Alternatively, one colorimetric test may require multiple specified testing areas, n, and require that all of the multiple specified testing areas n indicate as positive before an overall positive test result is indicated. By requiring a specified number of positive indicating pixels within each testing area and a specified number of testing areas indicating a positive result, the accuracy of a colorimetric test is greatly enhanced. Likewise, the number of false-positive results is greatly reduced as the subjectivity of interpreting such colorimetric test results is minimized.

At 805, the overall results of the colorimetric test is outputted from the colorimetric intensity analyzer 700 via output device 140. For example, the information output device 140 can be any display device to present or show the information, including, for example, a monitor, a screen, a holographic display, a projection display, a three-dimensional display, and the like.

As another example, the information output device 140 can include a plurality of light emitting diodes, with each of the light emitting diodes corresponding to a different value or outcome of the test. The system 100 can illuminate one or more light emitting diodes to convey information regarding the determined test result.

As yet another example, the information output device 140 can include a printer to print information, a speaker to audibly output information, a memory for storing the information and/or a network interface to transmit information regarding the assessed specimen validity characteristic to one or more remote devices or systems via network 105.

It is understood that the colorimetric intensity analyzer 700 may be used with or without the specimen validity analyzer 122 previously discussed.

Those of skill in the art will recognize that many of the methods or algorithms set out herein may employ additional acts, may omit some acts, and/or may execute acts in a different order than specified.

The various embodiments described above can be combined to provide further embodiments. To the extent that they are not inconsistent with the specific teachings and definitions herein, all of the commonly assigned U.S. patents, U.S. patent application publications, U.S. patent applications referred to in this specification, including but not limited to U.S. Provisional Patent Application No. 62/111,418, filed Feb. 3, 2015; U.S. Non-Provisional patent application Ser. No. 15/014,920, filed Feb. 3, 2016; and U.S. Provisional Patent Application No. 62/369,588, filed Aug. 1, 2016 are incorporated herein by reference, in their entirety. Aspects of the embodiments can be modified, if necessary, to employ systems, circuits and concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A specimen analysis system to analyze specimen test articles that include a plurality of testing areas that indicate at least a presence or an absence of a test subject compound in a specimen, the specimen analysis system comprising:
   at least one processor; and
   at least one non-transitory processor-readable medium that is communicatively coupled to the at least one processor and that stores at least one of processor-executable instructions or data that, when executed by the at least one processor, cause the at least one processor to:
      receive a set of image information that represents an image of each of the plurality of testing areas, each of the testing areas represented by a respective plurality of pixels in the set of image information;
      for each of the plurality of testing areas, determine a number of pixels that indicate as one of either the presence or the absence of the test subject compound;
      for each of the testing areas, determine if the number of pixels that indicate one of either the presence or the absence of the test subject compound equals or exceeds a first minimum threshold value which indicates that the testing area is positive for one of either the presence or the absence of the test subject compound;
      determine a number of testing areas that indicate positive for one of either the presence or the absence of the test subject compound; and
      determine if the number of testing areas that indicate positive for one of either the presence or the absence of the test subject compound equals or exceeds a second minimum threshold value which indicates an overall positive test result for one of either the presence or the absence of the test subject compound.

2. The specimen analysis system of claim 1, wherein to determine the positive indication of the plurality of pixels for one of either the presence or the absence of the test subject compound the processor assesses the intensity of a colorimetric change of the pixels.

3. The specimen analysis system of claim 2, wherein to assess the intensity of the colorimetric change the processor assesses criteria taken from the group consisting of hue, saturation and brightness or any combination thereof.

4. The specimen analysis system of claim 2, wherein the specimen test article includes a colorimetric specimen test.

5. The specimen analysis system of claim 4, wherein the colorimetric specimen test is a Guaiac test.

6. The specimen analysis system of claim 5, wherein the test subject compound is hemoglobin, the plurality of pixels are determined to indicate as positive in the presence of the hemoglobin, wherein the plurality of pixels are blue in the presence of the hemoglobin.

7. The specimen analysis system of claim 1, wherein the plurality of testing areas is six.

8. The specimen analysis system of claim 7, wherein five of the six testing areas must be respectively determined to indicate as positive for one of either the presence or the absence of the test subject compound to achieve an overall positive test result indicating the presence or the absence of the subject test compound.

9. The specimen analysis system of claim 1, wherein all of the plurality of testing areas must be determined to indicate as positive for one of either the presence or the absence of the test subject compound to achieve an overall positive test result indicating the presence or the absence of the subject test compound.

10. The specimen analysis system of claim 1, wherein each specimen test article further includes an optical specimen validity marker, the color of which indicates the validity of the specimen.

11. The specimen analysis system of claim 10, wherein the processor receives an image of the optical specimen validity marker and determines the validity of the specimen based upon the color of the pixels in the image.

12. A computer-implemented method to analyze specimen test articles that include a plurality of testing areas that indicate at least a presence or an absence of a test subject compound in a specimen, the method comprising:

receiving, by one or more computing devices, a set of image information that represents an image of each of the plurality of testing areas, each testing area represented by a respective plurality of pixels in the set of image information; and for each of the testing areas determining, by the one or more computing devices, a number of pixels that indicate as one of either the presence or the absence of the test subject compound;

for each of the testing areas determining, by one or more computing devices, if the number of pixels that indicate as one of either the presence or the absence of the test subject compound equals or exceeds a first minimum threshold value which indicates that the testing area is positive for one of either the presence or the absence of the test subject compound;

determining, by the one or more computing devices, a number of testing areas that indicate positive for one of either the presence or the absence of the test subject compound; and determining, by the one or more computing devices, if the number of testing areas that indicate positive for one of either the presence or the absence of the test subject compound equals or exceeds a second minimum threshold value which indicates an overall positive test result for one of either the presence or the absence of the test subject compound.

13. The computer-implemented method of claim 12, further comprising determining, by the one or more computing devices, the positive indication of the plurality of pixels for one of either the presence or the absence of the test subject compound by assessing the intensity of a colorimetric change of the pixels.

14. The computer-implemented method of claim 13, wherein assessing, by the one or more computing devices, the intensity of the colorimetric change includes assessing criteria taken from the group consisting of hue, saturation and brightness or any combination thereof.

15. The computer-implemented method of claim 12, further comprising:

assessing, by the one or more computing devices, the presence or the absence of the test subject compound based upon a colorimetric test.

16. The computer-implemented method of claim 15, wherein assessing the presence or absence of the test subject compound in the colorimetric test comprises assessing a Guaiac test for the presence or the absence of hemoglobin.

17. The computer-implemented method of claim 16, further comprising determining, by the one or more computing devices, the number of pixels within each testing area as indicating positive in one of either the presence or the absence of the hemoglobin.

18. The computer-implemented method of claim 12, wherein determining, by the one or more computing devices, the number of testing areas indicating one of either the presence or the absence of the subject test compound includes determining, by the one or more computing devices, the presence or the absence of the subject test compound in six testing areas.

19. The computer-implemented method of claim 18, wherein determining, by the one or more computing devices, the overall positive test result for one of either the presence or the absence of the subject test compound includes determining, by the one or more computing devices, that five of the six testing areas are indicated as positive for one of either the presence or the absence of the subject test compound.

20. The computer-implemented method of claim 12, wherein determining, by the one or more computing devices, the overall positive test result for one of either the presence or the absence of the subject test compound includes determining, by the one or more computing devices, that all of the testing areas are indicated as positive for either the presence or the absence of the subject test compound.

* * * * *